United States Patent [19]

Cohen et al.

[11] Patent Number: 4,998,975
[45] Date of Patent: Mar. 12, 1991

[54] TRAVENOUSLY PLACED DEFIBRILLATION LEADS

[75] Inventors: Donald M. Cohen, Irvine; James R. Thacker, Canyon Country, both of Calif.

[73] Assignee: Siemens-Pacesetter, Inc., Sylmar, Calif.

[21] Appl. No.: 429,440

[22] Filed: Oct. 30, 1989

[51] Int. Cl.$^5$ .............................................. A61N 1/00
[52] U.S. Cl. ........................... 128/419 D; 128/419 P; 128/784
[58] Field of Search ............... 128/419 D, 419 P, 784, 128/785, 786, 639, 642

[56] References Cited

U.S. PATENT DOCUMENTS

| | | | |
|---|---|---|---|
| 3,866,615 | 2/1975 | Hewson | 128/419 D |
| 3,942,536 | 3/1976 | Mirowski et al. | 128/419 D |
| 4,030,509 | 6/1977 | Heilman et al. | 128/419 D |
| 4,161,952 | 7/1979 | Kinney et al. | 128/786 |
| 4,270,549 | 6/1981 | Heilman | 128/784 |
| 4,291,707 | 9/1981 | Heilman et al. | 128/784 |
| 4,355,646 | 10/1982 | Kallok et al. | 128/786 |
| 4,522,212 | 6/1985 | Gelinas et al. | 128/419 P |
| 4,548,203 | 10/1985 | Tacker, Jr. et al. | 128/419 D |
| 4,567,900 | 2/1986 | Moore | 128/784 |
| 4,603,705 | 8/1986 | Speicher et al. | 128/786 |
| 4,628,937 | 12/1986 | Hess et al. | 128/642 |
| 4,641,656 | 2/1978 | Smits | 128/419 D |
| 4,662,377 | 5/1987 | Heilman et al. | 128/419 D |
| 4,727,877 | 3/1988 | Kallok | 128/419 D |
| 4,774,952 | 10/1988 | Smits | 128/419 D |
| 4,815,469 | 3/1989 | Cohen et al. | 128/634 |
| 4,817,634 | 4/1989 | Holleman et al. | 128/784 |
| 4,865,037 | 9/1989 | Chin et al. | 128/419 D |
| 4,946,457 | 8/1990 | Elliott | 128/419 D |

Primary Examiner—Francis Jaworski
Assistant Examiner—George Manuel
Attorney, Agent, or Firm—Bryant R. Gold; Lisa P. Weinberg; Leslie S. Miller

[57] ABSTRACT

A cardiac defibrillation system and method includes an epicardial electrode for making electrical contact with the epicardium from a position within the pericardial space, an endocardial electrode for making electrical contact with the endocardium of the heart, and means for making electrical contact with the epicardial and endocardial electrodes. The endocardial electrode is inserted transvenously into the heart in conventional manner. The epicardial electrode is also inserted transvenously into the heart, through the heart wall, and into the pericardial space. No open chest surgery is required.

30 Claims, 5 Drawing Sheets

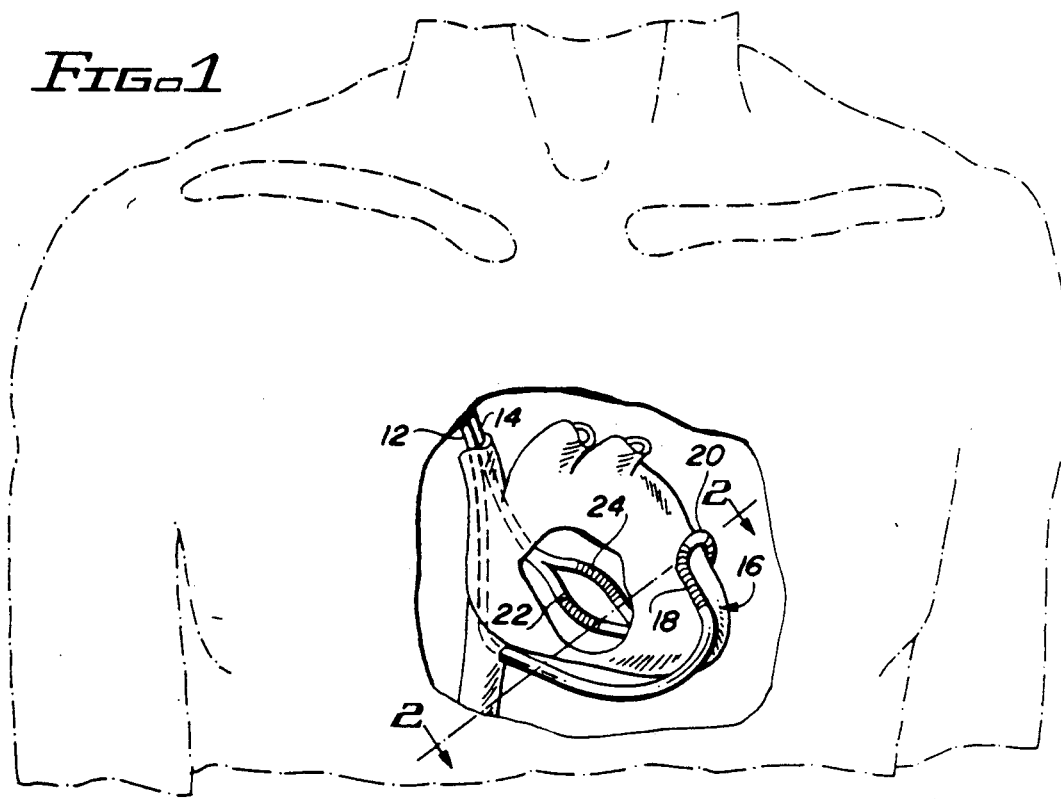
FIG. 1
FIG. 2
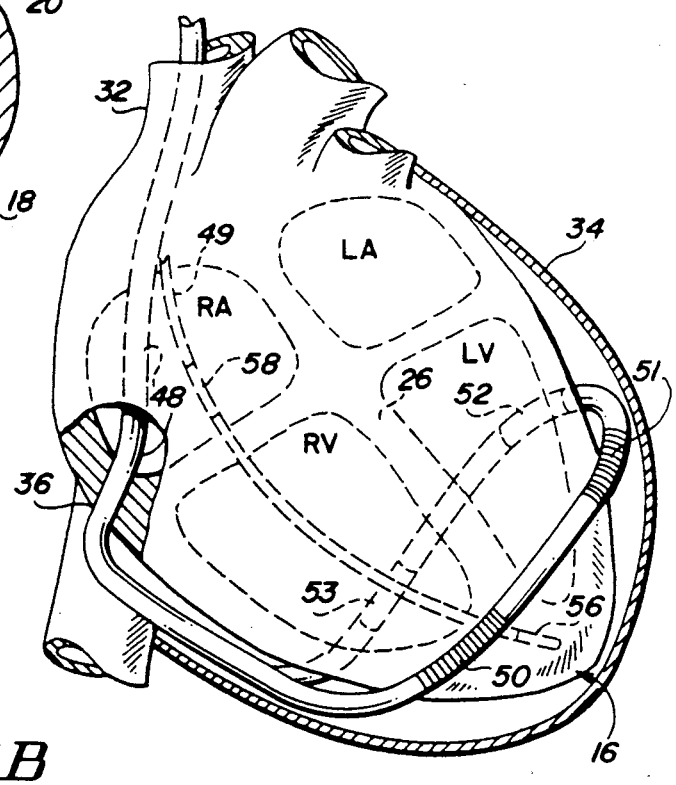
FIG. 3B

4,998,975

TRAVENOUSLY PLACED DEFIBRILLATION LEADS

BACKGROUND OF THE INVENTION

The present invention relates to implantable defibrillation leads and electrodes, and more particularly to methods for the transvenous placement of defibrillation electrodes.

A defibrillation device provides an electrical stimulus to a patient in an area near, on, or in the heart, for the purpose of reviving a heart that is not beating in a manner sufficient to sustain life. While there are numerous medical terms that can be used to describe such a heart, such as cardiac arrest, ventricular fibrillation, and asystole, and while each term has a somewhat different technical meaning, all are serious conditions that must be corrected immediately to prevent death of the patient. Hence, the defibrillation device is used in an attempt to get the heart beating again. To this end, a high energy stimulation pulse is delivered to, or near, the heart through one or more defibrillation leads, each lead having one or more electrodes at the distal end thereof. The present invention is concerned primarily with defibrillation leads, and with a manner of positioning the electrodes of such leads on or near the heart so that they can provide the greatest benefit Early defibrillation devices were large and cumbersome units that included a set of paddles, connected to a source of stored electrical energy through large wires. The paddles were positioned on the chest of the patient, typically by a doctor or paramedic, and the stored electrical energy was discharged one or more times through the paddles into the patient's body tissue. While such large defibrillation devices provided, and continue to provide, a measure of life support in emergency situations, such support can only be provided if a physician or paramedic having access to such a device is present.

It was recognized early that a defibrillation device could be carried by the patient at all times, i.e., the defibrillation device could be made portable and adapted to respond automatically to a stopped heart. With such a portable device, the needed life-sustaining defibrillation pulses could be automatically provided to the patient even in the absence of a physician or paramedic. One such early portable defibrillation device is disclosed in U.S. Pat. No. 3,866,615. The '615 patent teaches a lightweight, portable cardiac emergency stimulator that includes separate defibrillation and pacemaker electronic circuits. The leads and electrodes used with the portable device are introduced into the patient's heart by a needle through the chest wall.

Implantable defibrillation devices have also been developed, as shown in U.S. Pat. No. 3,942,536. Such devices offer the advantages of the portable device without the need for introducing leads through the chest wall. In the '536 patent, defibrillation leads having endocardial electrodes are introduced transvenously into the inside of the heart, similar to the leads used by implantable pacemakers. Other attempts at using transvenous defibrillation leads having endocardial electrodes have also been made, as shown for example in U.S. Pat. Nos. 4,161,952 and 4,355,646.

The advantages of providing an implantable automatic defibrillator in certain patients at high risk of experiencing ventricular fibrillation or other heart disorders are thus readily apparent. When fibrillation or related heart malfunctions are sensed by such devices, a large defibrillation shock is automatically delivered to the heart in an attempt to stimulate the heart back to a normal or near normal beating pattern. The life-saving defibrillation shocks are delivered without any undue delay, as would otherwise exist if external defibrillation pulses had to be delivered by paramedics (or other medical personnel) who were summoned to the aid of a heart-failing patient.

One of the main problems associated with defibrillating a heart (replacing a dangerous rhythm with a more normal one) with an electrical stimulus, however, is that a relatively large surface area of the myocardial tissue, typically ventricular myocardial tissue, must be stimulated in order to overcome fibrillation. Some of the energy is naturally expended on body fluids and tissues other than the myocardium. Hence, more energy must usually be delivered over a larger tissue area than would otherwise be required.

Prior art defibrillation leads and electrodes have generally been concerned with the size and shape of the surface area of the electrodes and correctly positioning the electrodes relative to the heart. Typically, at least a pair of such electrodes are positioned relative to the myocardial tissue so that the defibrillating electrical energy passes through the appropriate myocardial tissue and the amount of energy delivered to other tissues is minimized. U.S. Pat. Nos. 4,030,509; 4,291,707; and 4,548,203 are representative of such efforts. Unfortunately, placement of relatively large electrodes on the exterior of the heart, i.e., epicardial electrodes, has usually required open chest surgery—a difficult and somewhat risky procedure at best. Placement of large electrodes within the heart could potentially impair cardiac function or contribute to thrombosis and/or emboli formation in the heart.

One problem associated with placement of epicardial defibrillation electrodes is that the heart resides in the pericardium. The pericardium is a membranous sac that encloses the heart. It consists of an outer layer of dense fibrous tissue, with an inner serous layer (the epicardium) which directly surrounds the heart. Thus, in order to make direct contact with the epicardial tissue, and thereby be as close as possible to the myocardial tissue, the pericardium must somehow be pierced Again, this has usually required open-chest surgery. Other techniques for gaining access to the heart have been proposed. See, e.g., U.S. Pat. No. 4,270,549; and applicant's copending U.S. patent application, "SubXiphoid Positioning of Epicardial Defibrillation Electrodes and Electrode Anchoring Means," filed Apr. 4, 1989, as Ser. No. 07/333,391, which application is incorporated herein by reference.

Because of the problems associated with placement of epicardial electrodes, the concept of a transvenously implanted defibrillation lead and endocardial electrode remains an attractive alternative to open-chest surgery. Unfortunately, to date transvenous placement of defibrillation leads and electrodes (acting alone or in concert with subcutaneous electrodes) has proven unsatisfactory because the electrode surface area can not be made large enough for energy efficient cardiac defibrillation. Most prior uses of transvenous defibrillation leads with their resulting endocardial electrodes have thus been limited to uses in combination with epicardial electrodes, as shown for example in U.S. Pat. No. 4,641,656. (In this regard, it should be noted that the amount of energy required to defibrillate a typical fibrillating heart is much larger than the energy required to stimulate a nonfibrillating heart, as is used for example, by a pacemaker.) What is needed, therefore, is a technique for transvenously placing defibrillation leads having epicardial electrodes thereby avoiding the trauma and potential problems of open chest surgery.

Epicardial electrodes are preferred because their use generally minimizes the energy of a defibrillation pulse, and thereby improves the efficacy of the defibrillation system. Epicardial electrodes are in direct contact with the heart tissue. Further, epicardial electrodes cover large and strategic areas of the heart, thereby allowing the delivered electrical energy to be efficiently distributed throughout the fibrillating region. Such epicardial electrodes are typically placed around the exterior of the heart within the pericardial space. Because of the large surface area covered by many of these electrodes, they are sometimes referred to as "patch electrodes", often resembling patches that are placed on the heart. Although there are some shortcomings associated with placement of defibrillation electrodes directly on the epicardial surface, the advantages are overwhelming.

Unfortunately, however, as has been indicated, pericardial placement of defibrillation leads is a dangerous and difficult procedure that has heretofore generally required traumatic and endangering surgery, usually open-chest surgery. Needless to say, not all patients are suitable candidates for open-chest surgery, and even for those that are, the risks, trauma, and danger associated with such surgery make this procedure of electrode placement less than ideal. Hence, there is a need, as indicated above, for placement of epicardial electrodes in the propitious pericardial space without having to resort to dangerous open-chest surgery.

In an attempt to minimize the problems associated with open-chest surgery for the placement of epicardial defibrillation leads, it has been suggested to implant epicardial defibrillation leads transvenously. Such an approach is described in patent application Ser. No. 07/128,326, filed 12/03/87, entitled "Method For Transvenous Implantation of Objects into the Pericardial Space of Patients," of which the applicant named herein is a co-inventor. This prior application, including the methods and leads described therein (hereafter referred to as the "transvenous implantation approach"), is incorporated by reference herein.

In accordance with the transvenous implantation approach described in the above-referenced prior application, a guide wire and a catheter are inserted into the heart transvenously, with the aid of an introducer, as required. Once in the heart, the right atrial lateral wall is punctured, making a hole therein, through which a non-deployed defibrillation electrode is inserted, thereby entering the pericardial space. The nondeployed electrode is further positioned within the pericardial space to a desired position, and then the electrode is deployed so as to better contact a larger surface area of the outside of the heart.

The transvenous implantation approach offers a very viable alternative to open chest surgery. However, because the transvenous approach is generally limited to an introducer not much larger than a Fr 14 (a Fr 14 instrument is approximately 4.7 mm in diameter), and because the introducer's path is somewhat tortuous, some severe restrictions are imposed on the geometry and flexibility of the electrode and the deployment system that may be used therewith As a result, only small, easily deployed lead systems can be used effectively with the transvenous implantation technique. Unfortunately, a lead system having a small deployable electrode may not be sufficient for many patients in need of an implantable automatic defibrillator. What is needed, rather, is a transvenously implantable defibrillation lead having a large electrode surface area, or equivalent, wherein the advantages of the transvenous implantation technique can be exploited to avoid the trauma of open-chest surgery while still allowing at least one electrode surface area to be placed in the propitious pericardial space. The present invention advantageously addresses this and other needs.

SUMMARY OF THE INVENTION

The present invention provides a cardiac defibrillation system and method that includes an epicardial electrode for making electrical contact with the epicardium of the heart from a position within the pericardial space. Also included in some embodiments is an endocardial electrode for making electrical contact from within a chamber of the heart. Conventional means for making electrical contact with the epicardial and endocardial electrodes are further included. The endocardial electrode is inserted transvenously into the heart in conventional manner, similar to the manner of inserting a pacemaker lead into the heart. The epicardial electrode is also inserted transvenously into the heart, whereupon a small hole is punctured through the heart wall, allowing the epicardial electrode to be inserted into the pericardial space. Advantageously, no open chest surgery is required In a preferred embodiment, the epicardial electrode comprises a plurality of electrodes that are electrically connected together, yet spaced apart along the length of an elongate, insulated, flexible electrical conductor. This elongate conductor is inserted through a small hole made in the right atrial lateral wall and, using conventional lead positioning means (well known in the pacemaker and medical art), is positioned around the epicardial tissue at desired locations, with each of the plurality of electrodes making contact with the epicardial tissue at desired locations. No deployment of any large area electrodes is required, and no complex electrode deployment systems are needed. Rather, the length and number of each electrode on the elongate conductor provide the equivalent of a large area electrode.

Advantageously, the hole made in the heart wall need be no larger than necessary to allow insertion of the elongate conductor. In contrast, the hole made using the transvenous implantation approach of the prior art must be sufficiently large to allow a patch electrode and related deployment mechanism to pass therethrough.

The present invention may be characterized, in accordance with one embodiment thereof, as a cardiac defibrillation system that includes: (1) an epicardial electrode for making electrical contact with the epicardium of a human heart from a position within the pericardial space of the heart; (2) means for transvenously inserting the epicardial electrode into the pericardial space; (3) an endocardial electrode for making electrical contact with the endocardium of the heart; (4) means for making electrical contact with the epicardial and endocardial electrodes; and (5) means for selectively placing a momentary electrical potential between the epicardial and endocardial electrodes through the electrical contact means. The electrical potential causes a momentary electric field to exist between the epicardial and endocardial electrodes, and this electric field also exists throughout the heart. It is this electric field that causes the myocardium to be depolarized (excited) and to thereby contract.

The invention may further be characterized as an implantable defibrillation lead that comprises: (1) an epicardial electrode for making physical contact with the epicardium of a human heart from a position within the pericardial space of the heart, this epicardial electrode being transvenously insertable into the pericardial space; (2) an endocardial electrode for making physical contact with the endocardium of the heart; and (3) means for making electrical contact with the epicardial and endocardial electrodes. When an electrical potential of sufficient magnitude is placed between the epicardial and endocardial electrodes by way of the electrical contact means, the depolarization of myocardial tissue proximate the electrodes is triggered.

The invention also is directed to a method of defibrillating a human heart. This method includes the steps of: (a) transvenously inserting an epicardial electrode into the pericardial space surrounding the heart; (b) positioning the epicardial electrode so that it makes electrical contact with a desired area of the epicardium; (c) transvenously inserting an endocardial electrode inside of the heart; (d) positioning the endocardial electrode so that it makes electrical contact with a desired area of the endocardium; and (e) applying an electrical potential between the epicardial and endocardial electrodes, which electrical potential triggers the depolarization of myocardial tissue proximate the epicardial and endocardial electrodes.

In accordance with one aspect of the invention, a defibrillation lead system is provided that includes both epicardial and endocardial electrodes. A feature of the invention is that the leads used in such a system, including both the epicardial and endocardial electrodes, may be implanted transvenously without the necessity of open-chest surgery.

In accordance with another aspect of the invention, a transvenously insertable defibrillation lead having at least one epicardial electrode is provided wherein no intricate deployment equipment or methods are required in order to position the electrode at a desired epicardial location. Further, a sufficiently large surface area of epicardial tissue is contacted by the epicardial electrode(s) so as to allow an efficient use of electrical energy in effectuating cardiac defibrillation. Large surface area patch configurations are not required, which patch configurations could not be safely inserted transvenously into the pericardial space as are the epicardial electrodes of the present invention.

It is another aspect of the invention to provide such a defibrillation lead wherein the electrodes are fabricated to prevent excessively high current densities, which high current densities could burn the cardiac tissue with which the electrodes come in contact.

It is still another aspect of the invention to provide a defibrillation lead as above-described wherein the relative locations of the endocardial and epicardial electrodes can be selectively positioned relative to critical myocardial tissue so as to minimize the electrical potential required to defibrillate the heart.

It is yet another aspect of the invention, in accordance with one embodiment thereof, to provide a defibrillation electrode system and method wherein the relative concentration of defibrillation energy can be directed to different areas of the myocardial tissue without physical movement of the electrodes.

A still further aspect of the invention is to provide such an electrode system and method wherein periodic or other measurements of certain physiological parameters are measured and used as feedback to control the allocation of defibrillation energy to the myocardial tissue.

Yet another aspect of the invention is to provide a single pass defibrillation lead having a plurality of electrodes, the internal construction of the lead determining in large part the relative amounts of defibrillation energy that are applied from each electrode to adjacent tissue for a given defibrillation potential applied between a plurality of such leads.

BRIEF DESCRIPTION OF THE DRAWINGS

The above and other advantages, aspects and features of the present invention will be more apparent from the following more particular description thereof, presented in conjunction with the following drawings, wherein:

FIG. 1 is a diagram illustrating the transvenously placed endocardial and epicardial defibrillation leads and electrodes of the present invention, the epicardial electrodes being positioned in the pericardial space of a heart, and the endocardial electrodes being positioned within the right ventricle of the heart, with a portion of the heart being cutaway in order to better illustrate the endocardial electrodes;

FIG. 2 is a simplified sectional representation of the heart taken generally along the line 2—2 of FIG. 1, and illustrates the relative placement of the endocardial and epicardial electrodes relative to the right and left ventricles of the heart;

FIGS. 3A-3E illustrate various alternative embodiments and placements of the endocardial and epicardial electrodes of the present invention;

DETAILED DESCRIPTION OF THE INVENTION

Figure 3A:
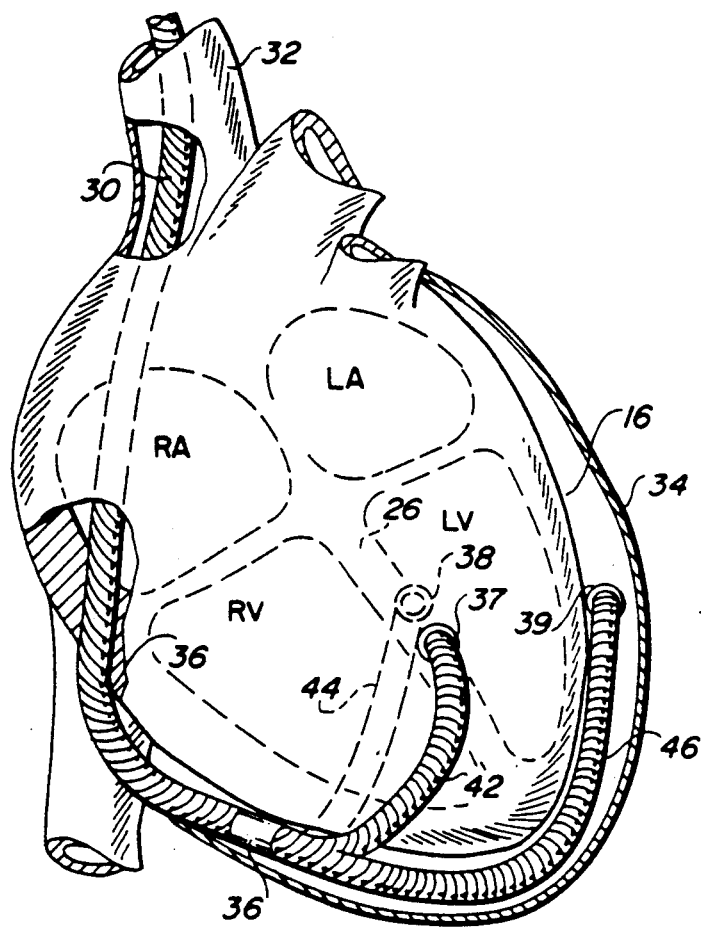

The following description is of the best presently contemplated mode of practicing the invention. This description is not to be taken in a limiting sense but is made merely for the purpose of describing the general principles of the invention. The scope of the invention should be ascertained with reference to the appended claims.

At the outset, it is noted that the drawings used herein are not intended to present an anatomically accurate nor detailed representation of a human heart and its surrounding pericardium, or of any other part or tissue location of the mammal. Rather, all of the drawings are presented in a very simplified format in order to emphasize the main features of the invention. Most anatomical and physiological detail has been omitted for clarity. However, it is also to be emphasized that the drawings have been selected and designed to provide sufficient detail to enable one skilled in the cardiac medical implantation arts to readily carry out and practice the present invention.

Further, it should be noted that all of the lead systems herein described are designed for transvenous placement. Indeed, one of the significant advantages of the present invention is the ability to place an effective defibrillation electrode configuration in contact with a human heart without the need for open-chest surgery. The methods and techniques used for such transvenous placement are known in the art or are described in other documents referenced herein. Hence, such methods and techniques will not be repeated in this application.

Further, all embodiments of the present invention utilize transvenous placement of at least one epicardial defibrillation electrode into the pericardial space surrounding the heart. The details of such transvenous placement are described in the referenced document and will not be repeated here. Essentially, such placement involves transvenously inserting a guide wire and a catheter into the heart, with the aid of an introducer, as required. Once in the heart, the atrial lateral wall of the heart is punctured to make a small hole therein. A defibrillation electrode is then inserted through the hole, thereby entering the pericardial space. The electrode is then positioned within the pericardial space to a desired position.

As indicated, this transvenous implantation technique is fully described in the documents incorporated by reference herein. It is noted that those documents describe the method and technique for use with a deployable defibrillation electrode. That is, in accordance with the teachings of those documents, once the hole has been made in the atrial wall, the electrode is inserted into the pericardial space while in a retracted (nondeployed) position. It is then moved to a desired position within the pericardial space, and then deployed so as to better contact a larger surface area of heart tissue. The teachings of those documents relating to the methods and techniques of transvenous implantation, puncturing the atrial wall, and positioning the nondeployed electrode are equally applicable to the present invention, and hence, as indicated, will not be repeated herein. It is significant to note, however, that one advantage that the present invention offers over that which is taught in the referenced documents is that the leads and electrodes inserted into the pericardial space in accordance with the present invention need not be larger than the lead diameter. Hence, the hole in the atrial wall for the present invention may be much smaller than the hole required for a non-deployed deployable electrode. This is a significant advantage. Further, because no deployment mechanisms are used, the lead may be more flexible at its distal end, and therefore more easily positioned to a desired location once within the pericardial space. This too is a significant improvement over the more rigid and stiff leads resulting from use with deployment mechanisms. Moreover, such flexibility advantageously results in less irritation to the tissue surrounding the heart.

One embodiment of the electrode configuration of the present invention is illustrated in FIG. 1. Shown in FIG. 1 is a patient 10 having an epicardial defibrillation lead 12 and an endocardial defibrillation lead 14 transvenously inserted so as to make contact with the patient's heart 16. The epicardial lead 12 enters the atrium of the heart transvenously, in conventional manner, and then exits through a small hole in the atrial lateral wall into the pericardial space (not shown in FIG. 1) surrounding the heart. The epicardial lead 12 is then looped around the heart tissue proximate the left ventricle. Included as an integral part of the lead 12 are two electrodes 18 and 20. In general, the lead 12 is as an elongate flexible electrical conductor, typically a helically wound conductor, having an electrically insulating sheath therearound. The electrical conductor and sheath comprise a lead body. The electrodes 18 and 20 are simply a segment of a conductive material having a circumference that is substantially the same as the circumference of the lead body. For example, the electrodes 18 and 20 may comprise spring electrodes that are simply an exposed (non insulated) section of the helically wound conductor that forms part of the lead 12. Other forms of electrodes are, of course, possible, such as electrodes similar to the "ring electrodes" used as part of a conventional pacemaker bipolar lead. As indicated, the electrodes are preferably made as an integral part of the lead body so that the overall diameter of the lead at the location of the electrode is not substantially larger than the diameter of the lead elsewhere.

Similar to the epicardial lead 12, the endocardial lead 14, for the embodiment shown in FIG. 1, includes two electrodes 22 and 24. The electrodes 22 and 24 form an integral part of respective branches of a distally bifurcated end of the lead 14. Many other configurations are possible for the endocardial electrodes, as discussed below.

For most applications, the epicardial electrodes 18 and 20 are electrically connected together by a single conductor within the lead 12. Similarly the endocardial electrodes 22 and 24 are electrically connected together by a single conductor within the lead 14. For some applications, e.g., sequential pulsing or selected energy pulsing, these electrodes may be electrically insulated from each other, each being connected to its own conductor within the respective lead.

The manner of making the implantable leads 12 and 14 is conventional. That is, as is well known in the pacemaker art, for example, the conductor of the leads is preferably a helically wound wire made from a suitable metal alloy that provides for good conductivity. This conductor is surrounded by an appropriate insulator, such as silicone rubber, with only the electrode portion exposed. The lumen through the center of the helically wound conductor provides a convenient access for inserting a stylet to aid during insertion of the lead to its desired position. If more than one conductor is required within the lead, two or more conductors may be helically wound coaxially, each having a different winding radius than the others, or the conductors may be placed side-by-side and helically wound on a common radius. In all instances, the conductors are electrically insulated from each other through the use of appropriate insulating sheath materials that are, in addition to being dielectrically appropriate, compatible with body fluids, such as silicone rubber. The conductors are helically wound as a spring in order to make the lead flexible without sacrificing the structural integrity of the conductor.

A better view of the preferred placement of the epicardial electrodes 18 and 20 relative to the endocardial electrodes 22 and 24 is shown in the sectional representation of the heart 16 shown in FIG. 2. As seen in FIG. 2, the endocardial electrodes 22 and 24 are preferably positioned so as to contact the septum 26 that separates the right ventricle (RV) of the heart form the left ventricle (LV) of the heart. The epicardial electrodes 18 and 20 are positioned so as to contact the myocardial tissue at respective locations on the epicardium of the heart. The four electrodes 18, 20, 22, and 24 thus are in very close proximity, at least in the particular sectional representation of the heart shown, to the respective quadrants of the left ventricle. That is, if in FIG. 2 an imaginary line were drawn from electrode 18 to electrode 20 to electrode 24 to electrode 22 and back to electrode 18, a four-sided polygon would be formed, with the left ventricle area substantially filling the area of the polygon. Such an electrode configuration as is shown in FIGS. 1 and 2 is frequently referred to as an orthogonal electrode placement.

Advantageously, an orthogonal electrode placement such as is shown in FIG. 2 allows the left ventricular myocardial tissue, which tissue comprises the bulk of the muscle tissue mass responsible for pumping blood from the heart, to receive most of the energy delivered from the electrodes. As a result, most of the ventricular myocardial tissue mass can be depolarized without requiring massive patch electrodes or thoracotomy (open chest surgery) for implant. It is noted that although the entire ventricular mass, or very nearly so, must be depolarized to reestablish a life sustaining rhythm, the left side generally requires more energy than the right side to depolarize, owing primarily to its larger mass and volume.

Referring next to FIG. 3A, a variation of the present invention is shown using just an epicardial lead 30. The lead 30 is transvenously inserted into the right atrium (RA) of the heart 16 by way of the superior vena cava 32 in conventional manner. The lead 30 passes through an opening 36 made in the lateral wall of the right atrium in accordance with the methods taught in the documents referenced above. The heart 16 is surrounded by the pericardium 34. The space between the heart 16 and the pericardium 34 is referred to as the "pericardial space". Typically, the pericardium 34 lies close to the epicardial heart tissue, so that the pericardial space is not very wide. In order to facilitate insertion of the lead 30 into the pericardial space, techniques are known for distending the pericardium from the heart, as taught, for example, in applicant's copending patent application "Sub-Xiphoid Positioning of Epicardial Defibrillation Electrodes and Electrode Anchoring Means," referenced above. For the embodiment shown in FIG. 3A, the lead 30 includes four electrodes 36, 37, 38 and 39. The electrode 36 is a ring electrode, or equivalent, that is positioned at a desired location along the length of the body of the lead 30. The other three electrodes 37-39 are positioned at the distal ends of respective branches 42, 44 and 46 of the lead 30. (It is noted that while three such electrodes and branches are shown in FIG. 3A, it is to be understood that any number of branches and electrodes could be employed, although as a practical matter it is unlikely that one would use more than four branches on such a lead.)

Advantageously, the electrode configuration shown in FIG. 3A utilizes electrodes that are much smaller than those used with a large patch electrode. Because of their small size, the electrodes can be inserted into the pericardial space with significantly less effort than is required to insert deployable patch electrodes into the same space. Further, their small size allows the respective branches or prongs of the lead 30, as well as the lead 30 itself, to be much less stiff, causing less local irritation to the patient. Further, and most significantly, because the lead 30 may be less stiff, there is less stress on the transcardial lead feedthrough site (the opening 36), thereby reducing the risk of complications developing at this site.

In order to place the electrodes shown in FIG. 3A, the lead 30 with its three branches or prongs are contained within a sheath (not shown). After making the transcardial feedthrough opening 36, in the manner described in the referenced documents, the sheath with the lead contained therein is inserted transvenously into the right atrium of the heart and through the opening 36. Once the sheath and lead are thus positioned within the pericardial space, the sheath is removed. The distal branches 42, 44 and 46 of the lead 30 are then further positioned within the pericardial space as desired. Such positioning may be accomplished, for example, by including respective stylets in the lead 30 during implant, each stylet terminating in its respective branch, and by using the corresponding stylet to place the branch at a desired location within the pericardial space. Once the appropriate branch of the lead is in a desired position, the stylet is removed.

Hence, in the manner described, the four electrodes 36-39 may be positioned in any desired location in contact with the epicardium. Typically, as shown in FIG. 3A, these electrodes will be positioned so as to surround the ventricles.

From a practical standpoint, and still with reference to FIG. 3A, the free walls of the ventricle can best be depolarized with the electrodes 36 and 39 in contact with the epicardium. However, the septum 26 can be depolarized effectively whether the electrodes 37 and 38 are epicardial or endocardial. Consequently, in order to simplify the construction of the epicardial lead, various other electrode configurations, utilizing both epicardial and endocardial leads, are contemplated. A preferred such configuration is illustrated in FIGS. 1 and 2 and is described above. Other possible configurations are illustrated in FIGS. 3B-3E.

FIG. 3B, for example, illustrates an embodiment of the present invention utilizing both an epicardial lead 48 and an endocardial lead 49. Both leads 48 and 49 are inserted transvenously into the heart. The epicardial lead 48 passes from the right atrium of the heart through a transcardial opening 36 into the pericardial space, as described above. The endocardial lead 49 passes through the right atrium into the right ventricle. The distal end of the epicardial lead 48 comprises a loop having four spaced-apart electrodes 50-53 thereon. This loop is positioned within the pericardial space so as to encircle the ventricles, with the electrodes 50-53 contacting epicardial tissue at roughly equally spaced locations around the ventricles. The distal end of the endocardial lead 49 includes two spaced-apart electrodes 56 and 58. As shown in the figure, electrode 56 is positioned at the distal tip of the lead 49 so as to be within the right ventricle, and electrode 58 is positioned along the length of the body of the lead 49 so as to lie within the right atrium. However, this positioning is only exemplary. Other relative positions for the electrodes could be utilized. For example, the endocardial electrode 58 may be positioned closer to the electrode 56 so that both electrodes 56 and 58 lie in the right ventricle.

Figure 3C:
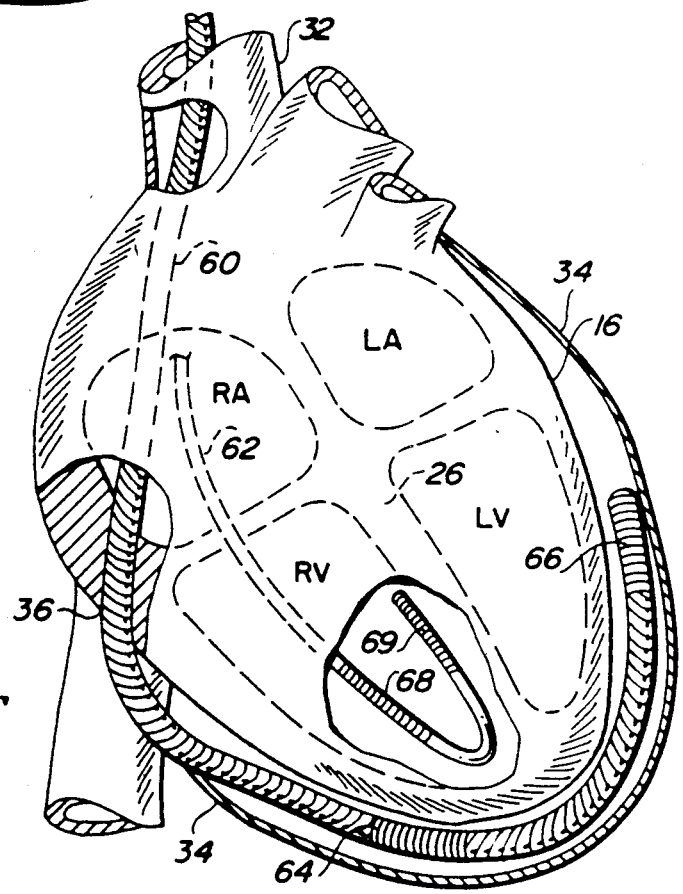

FIG. 3C depicts yet another embodiment of the electrode placement of the present invention. Like the embodiments of FIGS. 2 and 3B, this embodiment employs an epicardial lead 60 and an endocardial lead 62. The epicardial lead 60 is inserted transvenously into the pericardial space as described above. This epicardial lead 60 includes electrodes 64 and 66 spaced along the length of the body of the lead 60 so that each electrode makes contact with appropriate ventricular epicardial tissue. The endocardial lead 62 is configured as a J-lead, with electrodes 68 and 69 positioned on opposing segments of the "J". The electrodes 68 and 69 are preferably positioned within the right ventricle so as to make contact with the septum 26, similar to what is shown in the sectional representation of FIG. 2. (Note, as shown in the two dimensional representation of FIG. 3C, it appears that only the endocardial electrode 69 is in contact with the septum 26 and not the electrode 68. However, this is done simply to emphasize that there are two electrodes. To show both electrodes in contact with the septum 26 would mean that one electrode would block the view of the other electrode. Hence, the electrode 68 is shown as being away from the septum wall, when in actuality it is preferred that both endocardial electrodes contact the septum wall, one ventrally, one dorsally.)

Figure 3D:
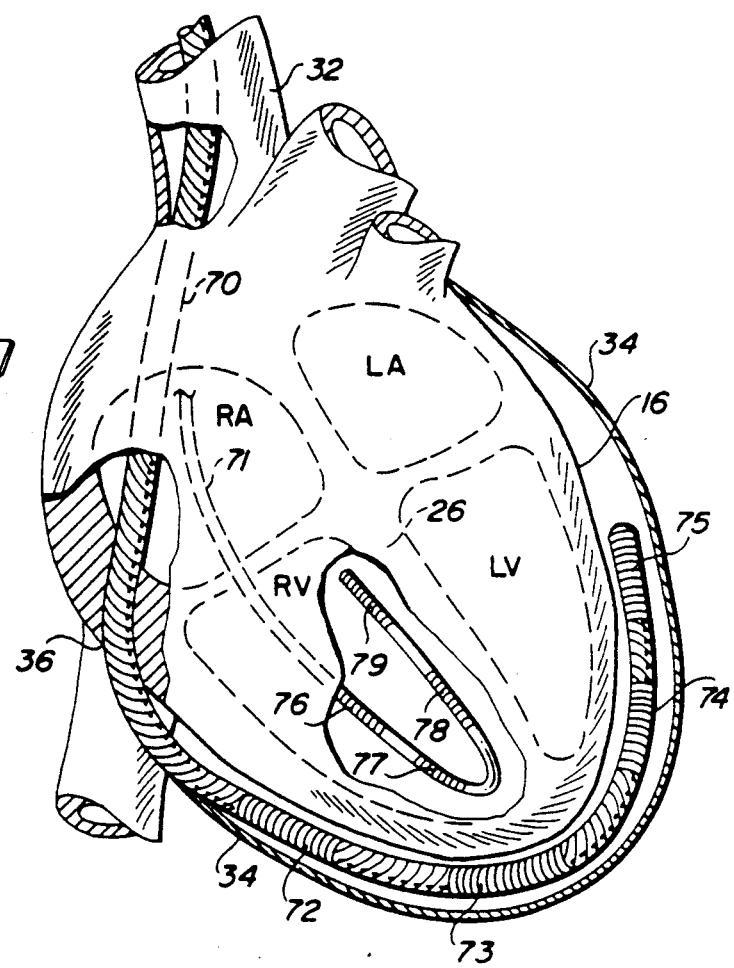

FIG. 3D illustrates yet another embodiment of the electrode placement of the present invention. This embodiment is very similar to the one described above in connection with FIG. 3C except that four electrodes, rather than two, are included on each of the epicardial and endocardial leads. That is, like the embodiment shown in FIG. 3C, the embodiment of FIG. 3D employs an epicardial lead 70 and an endocardial lead 71. The epicardial lead 70 is inserted transvenously into the pericardial space as described above. This epicardial lead 70 includes electrodes 72, 73, 74 and 75 spaced along the length of the body of the lead 70 so that each electrode makes contact with appropriate ventricular epicardial tissue. The distal end of the endocardial lead 71 is configured as a J-lead, with electrodes 76 and 77 being positioned opposite electrodes 78 and 79 on opposing segments of the "J". As with the description above (FIG. 3C) both segments of the "J" are preferably in contact with the septum wall 26, even through, as drawn, it appears only electrodes 78 and 79 are in contact with the septum wall. The embodiment of FIG. 3D makes better contact with a larger volume of ventricular tissue than does the embodiment of FIG. 3C, thereby providing a more effective means for depolarizing the ventricular myocardial tissue.

Figure 3E:
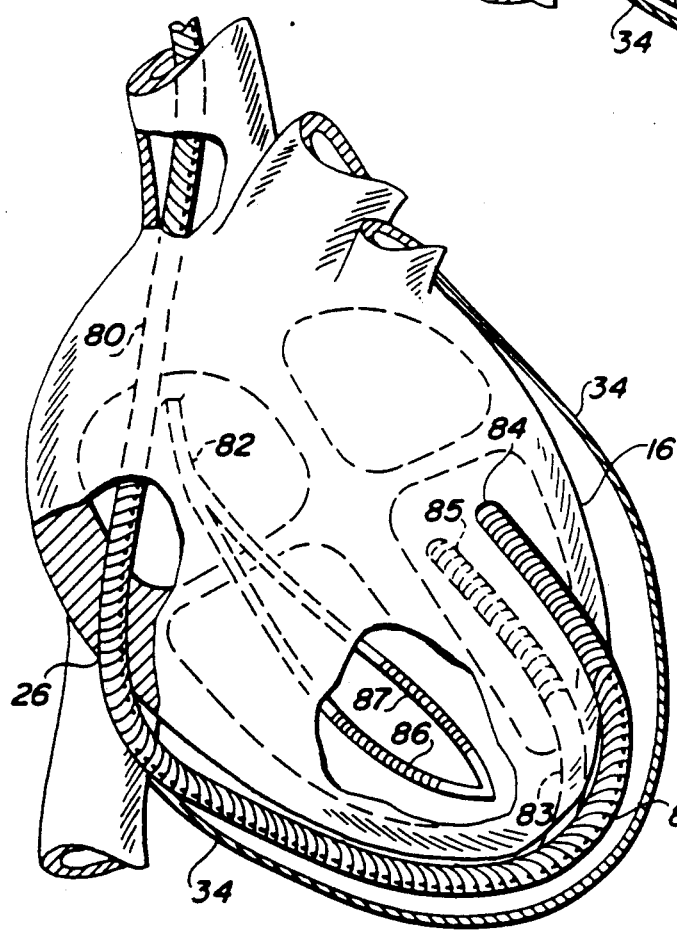

Referring next to FIG. 3E, yet another embodiment of the lead configuration is depicted. This embodiment likewise utilizes an epicardial lead 80 and an endocardial lead 82. The endocardial lead 82 is substantially the same as the endocardial lead 14 shown in FIGS. 1 and 2. That is, the distal end of the lead 82 is bifurcated, with each branch having an electrode 86 or 87 thereon. These electrodes are preferably positioned against the septum wall 26, the same as is shown in FIG. 2. The epicardial lead 80 includes a pair of prongs or segments 81 and 83, each of which includes at its tip an elongate electrode 84 and 85, respectively. These electrodes 84 and 85 are positioned within the pericardial space (using the transvenous insertion approach described above) so as to make contact with epicardial tissue of the left ventricle. The relative positioning of the electrodes of both leads 80 and 82 thus provides an orthogonal configuration, similar to that shown in FIG. 2, that effectively surrounds the left ventricle.

As indicated above, it is the massive myocardial tissue of the left ventricle that does most of the work in pumping the blood from the heart 16 throughout the body of the patient. For this reason, the electrode placement suggested in the sectional representation of FIG. 2, achieved, e.g., by lead/electrode configurations such as those shown in FIGS. 1 and 3E, or equivalent configurations, represents the preferred placement for many patients. Where a substantially orthogonal placement of the electrodes is achieved using these configurations, or equivalents thereof, the defibrillation energy is effectively distributed throughout the left ventricle so as to best depolarize the left ventricle.

For some patients, however, it may be difficult with this configuration to depolarize the right ventricle as well. Hence, an electrode configuration that directs more of the depolarization energy to the right ventricle while detracting from the left ventricle may be preferred. Such electrode configurations are taught, for example, in FIGS. 3A, 3B, 3C and 3D, or equivalents.

Figure 4A:
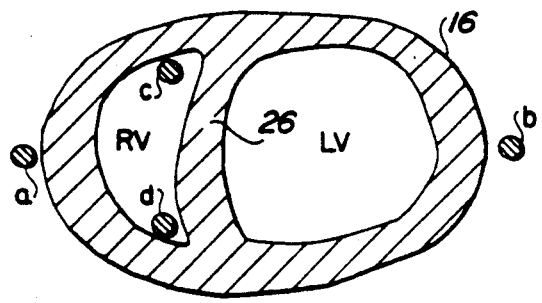
FIG. 4A is a sectional representation of the heart showing an alternative placement of the endocardial and epicardial electrodes relative to the right and left ventricles.

A sectional representation as would be seen through the ventricles of the heart 16 for these left-and-right ventricle electrode placement configurations (FIGS. 3A, 3B, 3C and 3D) is shown in FIG. 4A. In FIG. 4A, the epicardial electrodes are illustrated as dots (representative of the circular cross-sectional shape of the lead/electrode) identified by the reference letters "a" and "b", with electrode "a" being in contact with the epicardial tissue of the right ventricle, and electrode "b" being in contact with the epicardial tissue of the left ventricle, and further with the electrodes "a" and "b" being on opposite sides of the heart 16. Similarly, the endocardial electrodes shown in FIG. 4A are also represented as dots identified by the reference letters "c" and "d". Both electrodes "c" and "d" are positioned within the right ventricle so as to contact the septum wall 26. Preferably, these electrodes "c" and "d" are spaced apart so that they also are more or less on opposite sides of the heart 16. In this manner, the four electrodes a–d form a quasi-orthogonal arrangement that substantially encompasses both the right and left ventricles.

In a conventional use of the defibrillation electrodes a–d, a potential difference is placed on one set of electrodes, e.g., the epicardial electrodes "a" and "b", relative to the other electrodes, e.g., the endocardial electrodes "c" and "d". For example, +150 volts may be applied to electrodes "a" and "b", and −150 volts may be applied to electrodes "c" and "d". (Alternatively, 0 volts may be applied to one set of electrodes and −300 volts may be applied to the other set of electrodes, resulting in the same potential difference between the electrodes.) This potential difference, applied for just a short period of time, causes an electrical current, frequently referred to as a defibrillation pulse, to flow between the electrodes exhibiting the potential difference. It is this electrical current that triggers the desired depolarization of the cardiac tissue, thereby defibrillating the heart.

One possible difficulty with the electrode configuration shown in FIG. 4A is that the epicardial electrode "a" is by necessity closer to the endocardial electrodes "c" and "d" than is the other epicardial electrode "b". Hence, if voltage +V is applied to electrodes "a" and "b", and voltage −V is applied to "c" and "d", assuming the impedance presented by the cardiac tissue is roughly a function of the length of tissue involved, more current will flow to electrodes "c" and "d" from electrode "a" than flows from electrode "b". That is, where the same potential difference is applied between the endocardial and epicardial electrode sets, more defibrillation energy is directed to the right ventricle than is directed to the left ventricle.

Figure 4B:
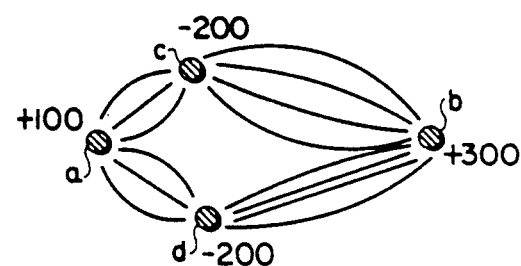
FIGS. 4B and 4C are iso-current and iso-potential maps, respectively, of the sectional representation of FIG. 4A assuming unequal potentials at the epicardial electrodes.
Figure 4C:
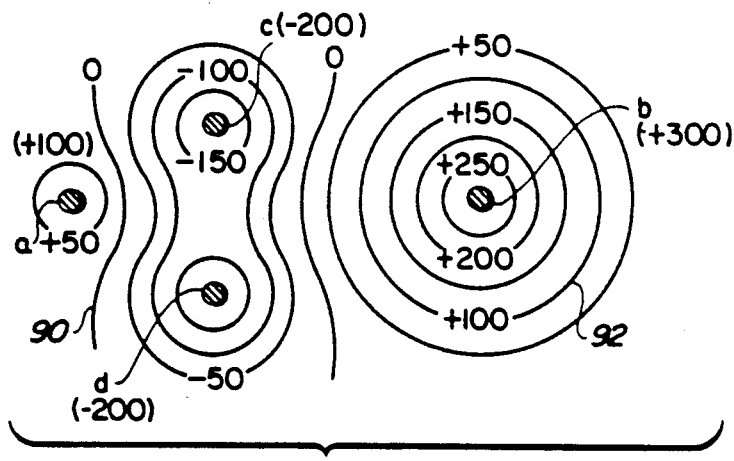

To depolarize the heart in an energy efficient manner, each portion of the heart should receive a voltage that is just above the voltage required to cause depolarization, i.e., just above the heart's threshold. To better distribute the defibrillation energy more uniformly throughout the heart, and particularly to the left ventricle, the present invention contemplates applying unequal potentials to the epicardial electrodes. For example, as shown in the iso-current map of FIG. 4B, which figure shows the four electrodes a-d of FIG. 4A, by applying a potential of +300 volts to electrode "b", a potential of +100 volts to electrode "a", and a potential of −200 volts to electrodes "c" and "d", the relative current density would be altered so that appropriate amounts of current flow through both the left ventricle tissue as well as the right ventricular tissue. This current flow is controlled by the relative potential difference between the respective sets of electrodes. This relative potential difference is illustrated in FIG. 4C, which figure depicts a representation of an iso-potential map for the electrode placement of FIG. 4A. FIG. 4C assumes potentials at each electrode as shown, i.e., +300 volts at electrode "b", +100 volts at electrode "a", and −200 volts at electrodes "c" and "d". The lines shown in FIG. 4C represent several loci of points for which the potential is the same. For example, the potential at line 90 between electrodes "a", "c", and "d" might be representative of a 0 potential iso-potential line, while the iso-potential line 92 around electrode "b" might be representative of a potential of +100 volts. With these potential differences, the current density that flows between the electrodes might be as illustrated by the iso-current density lines shown in FIG. 4B.

The above description highlights an important feature of the present invention: by controlling the potential applied to each electrode (and thereby controlling the potential difference between two or more electrodes), the distribution of the defibrillation energy within the heart can be selectively controlled. This principle applies to all of the electrode placements described herein, or equivalents thereof. Thus, even though two patients may have a similar electrode placement, the energy applied to different portions of their respective hearts may be different by simply adjusting the potential applied to the electrodes. Moreover, even for a single patient, the energy distribution can be altered as the needs and circumstances of the patient change, by such a simple voltage adjustment without requiring a physical relocation of the electrodes.

While use of the above described principle for controlling the distribution of defibrillation energy within the heart will typically require separate conductors within, e.g., the epicardial lead, thereby complicating the construction of such lead, it is noted that two-conductor leads are well known in the pacing art, such as the conventional bipolar lead. By making some minor adjustments to the construction of these leads, such as by selecting the insulating material used in the leads to have a high breakdown voltage, thereby electrically isolating the conductors from each other, even at the high voltage potentials used for defibrillation, this type of lead construction can readily be used for the leads of the present invention. Moreover, if desired, separate leads can be used for the electrodes "a" and "b", although where the electrodes "a" and "b" are the epicardial electrodes, it is generally preferred that only a single lead pass through the opening 26 of the atrial wall in gaining access to the pericardial space where the electrodes are positioned. However, in some instances, it may be just as easy, and no more irritable, for two very flexible thin leads to pass through the opening into the pericardial space as for one somewhat more stiffer and thicker lead to pass through the opening. Alternatively, for some patients it may also be more desirable to create two separate transmyocardial openings, one for each lead.

Figure 8:
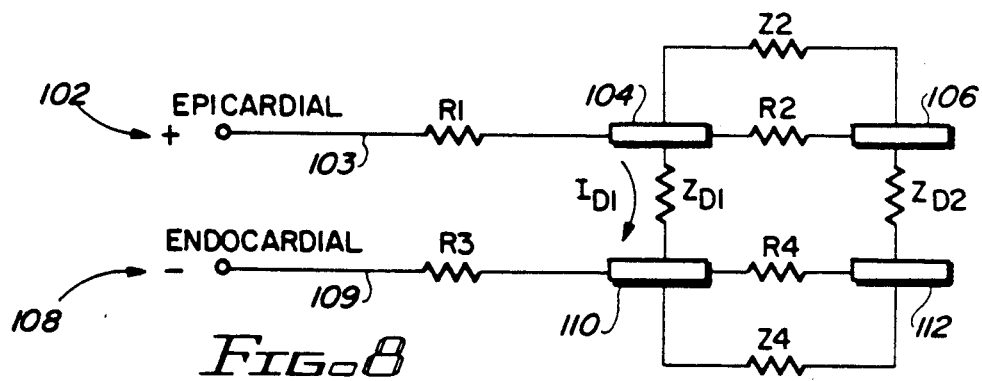
FIG. 8 is an equivalent electrical diagram of single-conductor epicardial and endocardial leads and electrodes, and illustrates the main defibrillation current that flows from one electrode of one lead to a corresponding electrode of the other lead as a result of a potential difference being applied to the conductors of each lead.

A further alternative is to use a specially constructed lead that has just a single conductor, and therefore can be made flexible and thin, and that yet allows different potentials to be applied to its respective electrodes. Such a lead is schematically illustrated in FIG. 8. In FIG. 8, an epicardial lead 102 includes an electrode 104 and an electrode 106. This lead includes a single conductor 103 having an effective resistance R1 between its proximal end and the electrode 104, and an effective resistance R2 between the electrode 104 and the electrode 106. The epicardial lead 102 is designed for use with an endocardial lead 108. The endocardial lead 108 also includes two electrodes 110 and 112. A single conductor 109 interconnects a proximal end of the lead with the electrode 110 and 112. This single conductor has an effective resistance R3 between the proximal end of the lead and the electrode 110, and an effective resistance R4 between the electrode 110 and the electrode 112. When the electrodes 104 and 106 are positioned in body tissue so as to be spaced apart from the electrodes 110 and 112, and when a potential difference is applied between the respective leads, the body tissue between the electrodes presents a path through which electrical current may flow. (For example, in FIG. 8, one such electrical path is represented as an impedance $Z_{D1}$ between the electrodes 104 and 110. Another path is represented as an impedance $Z_{D2}$ between the electrodes 106 and 112. Other electrical paths, e.g., between electrodes 104 and 112, and between electrodes 106 and 110, are not shown.) Hence, when a potential difference is applied between the leads 102 and 108, corresponding potential differences appear at the electrodes. The magnitude of these potential differences is determined by the magnitude of the various resistance values present in the circuit. In turn, the magnitude of the electrical currents that flow through the body tissue, such as the current $I_{D1}$ that flows through $Z_{D1}$, is determined by the potential differences among these electrodes. As is well known in the electrical art, the potential differences among the electrodes are determined by the values of the various resistances present in the circuit. Hence, by selectively designing a lead, such as the epicardial lead 102, to have a selected internal resistance R1 and R2, (done by proper selection of the conductive materials used in the lead), the relative values of the potentials appearing at the electrodes can be controlled.

That is, an effective voltage divider network is created by the lead construction in combination with the tissue impedance in order to develop a desired potential at each electrode. For example, by making R1 and R3 very small (e.g., just the normal resistance associated with a good metal conductor), and by making R2 and/or R4 much larger than R1 and R3, but still smaller than the parallel myocardial tissue impedance, Z2 and Z4, (by including appropriate resistive elements within the lead), a voltage divider network can be created that results in a significant difference between the potential appearing between electrodes 104 and 110 from that appearing between electrodes 106 and 112. In this manner, therefore, the amount of energy directed to the tissue locations represented by the respective impedances $Z_{D1}$ and $Z_{D2}$ can be controlled using a single conductor lead. Separate electrodes contained on further branches of a lead may also be designed for a variety of respective voltages by similar voltage dividers.

Figure 5A:
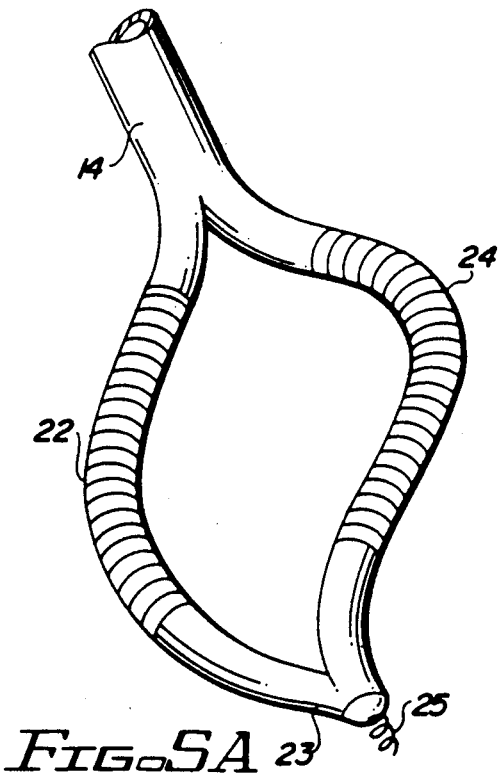
FIGS. 5A and 5B illustrate alternative configurations for the endocardial electrodes.

Referring next to FIG. 5A, an enlarged view of the bifurcated distal end of the endocardial lead 14 (FIG. 1) is illustrated. As shown, the distal end includes separate branches, each having a respective electrode 22 or 24 thereon. The ends of the branches are joined together at a tip 23. An active fixation mechanism, such as a screw-in helix 25, allows the tip 23 to be firmly secured to an appropriate location within the right ventricle. The lead is constructed so that the branches of the bifurcated section are spring loaded, thereby forcing these branches to assume a spaced-apart position relative to each other. This ensures an appropriate separation between the electrodes 22 and 24. During transvenous insertion of the lead, a sheath is used to hold in the spring-biased branches of the bifurcated end. The sheath remains over the lead until the lead is anchored to the tissue. The sheath is then removed, and the electrodes 22 and 24 spring out to their respective spaced-apart positions.

Figure 5B:
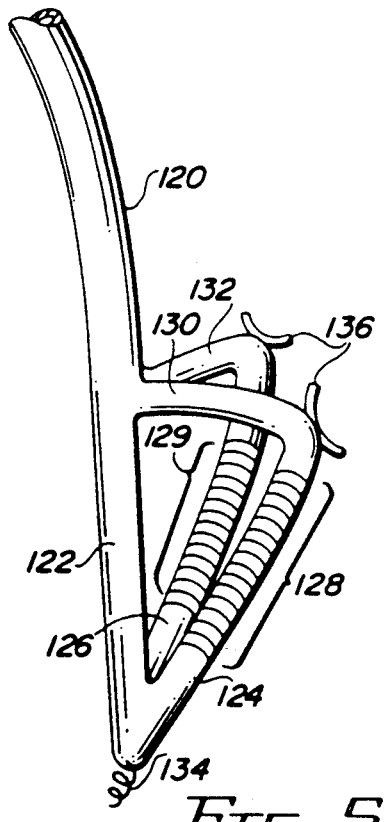

A further embodiment of the distal end of an endocardial lead 120 that could be used with the present invention is shown in FIG. 5B. The distal end of the lead 120 includes a main branch 122, and two side branches 124 and 126. Electrodes 128 and 129 are placed on the branches 124 and 126. The branch 124 loops back and joins the main body of the lead 120 with a very flexible lateral section 130. Similarly, the branch 126 loops back and joins the main body of the lead 120 with a very flexible section 132. The main branch 122 acts as a brace of sufficient stiffness to hold the electrodes 128 and 129 against the septum. The flexible sections 130 and 132 serve no electrical function, but are made entirely of silicone rubber, or other suitable body compatible material. During insertion of the lead 120, the branches 124 and 126 are folded back against the main branch 122, with the flexible sections 130 and 132 collapsing. This folded or collapsed position is maintained by holding the lead in a sheath. Once insertion has been made, the sheath is removed, and the branches 124 and 126 fold out to their extended position. An active fixation device, such as a helix screw 134, may optionally be used to firmly hold the tip of the lead to a desired tissue location within the right ventricle. Passive fixation means, such as fins 136 (or porous electrodes, not shown, in the area of fins 136) attached to the extremities of the branches 124 and 126, further help position and anchor the electrodes against the septum of the heart.

Figure 6A:
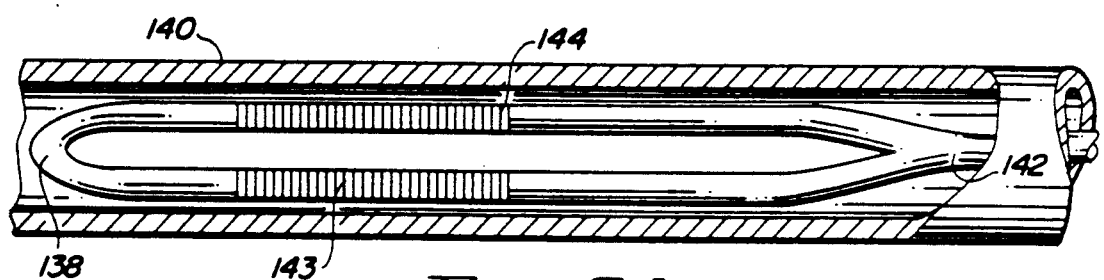
FIGS. 6A and 6B illustrate one embodiment of a epicardial defibrillation lead and electrodes while compressed within a sheath and removed from the sheath, respectively.
Figure 6B:
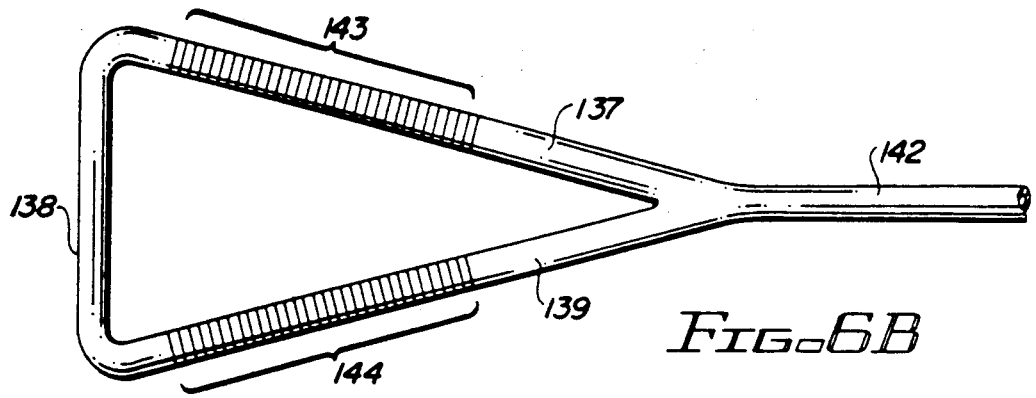

Referring next to FIGS. 6A and 6B, an enlarged view of one embodiment of an epicardial lead 142 is illustrated. This embodiment may be used, for example, in connection with the electrode configuration described above in connection with FIGS. and 2. In FIG. 6A, the lead 142 is held within a sheath 140. The lead remains within the sheath during the transvenous insertion of the lead into the pericardial space. Once the lead is positioned within the pericardial space, the sheath 140 is removed, and the end of the lead containing the electrodes opens up, as shown best in FIG. 6B. When opened, the distal portion of the lead comprises a loop, with branches 137 and 139 joined by a bridge 138. An electrode 143 resides on branch 137. Another electrode 144 resides on branch 139. The loop formed by the branches 137 and 139 and the bridge 138 is designed to fit around the left ventricle, as illustrated in FIG. If desired, fixation means may be used, such as a remote suture, for anchoring the lead to the pericardium in a plurality of locations.

Figure 7:
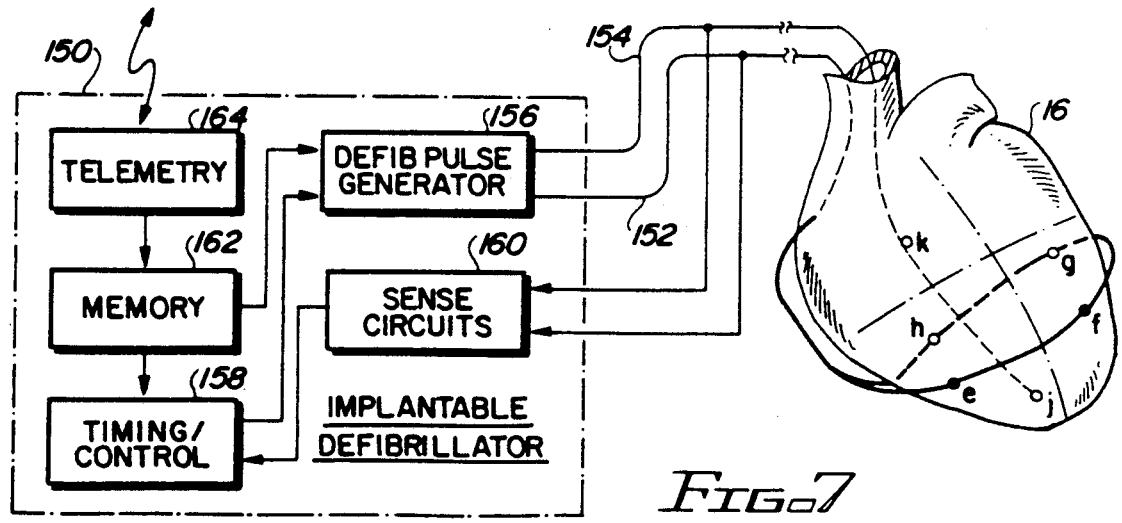
FIG. 7 is a block diagram of an implantable defibrillator coupled to various endocardial and epicardial defibrillation electrodes.

Referring next to FIG. 7, a simplified block diagram of an implantable defibrillator 150 is shown. The defibrillator 150 is connected to a heart 16 by way of an epicardial lead 152 and an endocardial lead 154. The epicardial lead shown in FIG. 7 includes four electrodes, identified by the letters "e", "f", "g" and "h". The endocardial lead includes two electrodes "j" and "k". (It is noted that the number of electrodes on each lead and their positions relative to the heart 16 are only exemplary, as any number of electrode configurations are possible as suggested, for example, by FIGS. 1-3.) The implantable defibrillator includes a defibrillation pulse generator 156 that generates the voltage potential between the electrodes of the epicardial and endocardial leads. This generator is controlled by a timing and control circuit 158. The timing and control circuit 158 generates appropriate trigger or control pulses that signal when the defibrillation pulses are to be applied by the pulse generator circuit 156 to the heart. A sense circuit 160 is also coupled to the endocardial lead 154 and detects cardiac activity in conventional manner. If the sense circuit fails to sense appropriate cardiac activity within a prescribed time, then such fact may be interpreted as a fibrillating or stopped heart, and a defibrillation pulse is delivered to the heart. If the heart does not respond within a prescribed time period, additional defibrillation pulses may be generated. The duration and amplitude of the defibrillation pulses, as well as the criteria for when such pulses are to be generated, are determined by appropriate control parameters stored in memory circuits 162. Advantageously, these parameters may be altered from time to time, as desired, through use of telemetry circuits 164. The manner in which such control parameters are altered is well known in the implantable pacemaker art.

In accordance with the present invention, the timing and control circuits 158 may be programmed or designed to provide selective voltage potentials to the defibrillation electrodes a–h and/or j–k for the purpose of directing the defibrillation energy to appropriate regions of the heart, as described above in connection with FIGS. 4A-4C. Further, as an additional feature of the present invention, the sense circuits can periodically, randomly, or selectively make various measurements relating to the interface between the electrodes and the myocardial tissue. For example, an impedance measurement can be made between respective electrodes, for the purpose of ascertaining where the defibrillation energy should be directed. A high impedance measurement would suggest a long stretch of myocardium between the electrodes, while a low impedance measurement would suggest a short stretch of myocardial tissue between the electrodes. Hence, such measurement could be used to signal that a high energy defibrillation pulse should be delivered in the former situation (good electrode position), while no energy or a low energy defibrillation pulse should be delivered in the latter situation (poor electrode position) to avoid expending energy in regions of heart where the energy would not be efficiently used to effectuate depolarization. This type of feedback information can thus be used to obviate the need for physical manipulation of the electrodes in order to achieve lower defibrillation thresholds.

It is thus seen that by using a programmable implantable defibrillator such as that shown in FIG. 7, a great deal of flexibility is provided in distributing and directing defibrillation energy to desired regions of the heart regardless of the particular electrode configuration that is used. For example, assume an electrode configuration such as is illustrated in FIG. 3B. The advantage of this particular epicardial configuration is that it is easier to place around the heart. The disadvantage is that it only concentrates energy at one level in the heart. To minimize the effects of this disadvantage, an endocardial lead is used having an electrode 58 in the right atrium and an electrode 56 in the right ventricle. Note that the electrodes 56 and 58 of FIG. 3B may correspond to the electrodes "j" and "k" of FIG. 7. Further, the electrodes 50-53 of FIG. 3B may correspond to the electrodes e-h of FIG. 7. By appropriate use of the electrodes "j" and "k", the defibrillation energy may be selectively pulled up or down within the myocardial tissue. For example, if a single defibrillation pulse is desired, electrodes "e", "g" and "j" could be made positive, and electrodes "f", "h" and "k" could be made negative. The respective amplitudes of the voltages on each electrode are then adjusted as above described in order to achieve a desired distribution. If, on the other hand, a sequential pulse sequence is desired, then "e", "g" and "j" can be made positive, and "f", "h" and "k" negative; followed by having "e", "g" and "k" positive, and "f", "h" and "j" negative. This sequence may continue as long as desired, in effect pulling energy up and down the heart, but not around the heart. Many other possibilities for sequencing are, of course, possible.

Thus, as described above, it is seen that the present invention provides a defibrillation lead system, including both epicardial and endocardial electrodes, wherein both the epicardial and endocardial electrodes may be implanted transvenously without the necessity of open-chest surgery. Advantageously, without the need for intricate deployment equipment or methods, a sufficiently large surface area of epicardial tissue is contacted by the epicardial electrode(s) so as to allow an efficient use of electrical energy in effectuating cardiac defibrillation. Moreover, the relative locations of the endocardial and epicardial electrodes can be selectively positioned relative to critical myocardial tissue so as to minimize the electrical energy required to defibrillate the heart. Further, once the electrodes are positioned in a desired configuration, the distribution of the defibrillation energy within the myocardial tissue may be selectively adjusted without physical movement of the electrodes by controlling the relative voltage potentials applied to each electrode. Such control can be guided by making periodic or other measurements of certain physiological parameters, the results of which measurements may thereafter be used as feedback to control the allocation of defibrillation energy to the myocardial tissue.

While the present invention has been described above by means of specific embodiments thereof, it should be understood that this description is given for illustrative purposes only and that many alterations and modifications may be practiced without departing from the spirit and scope of the invention. It is, therefore, the intent that the present invention not be limited to the above description, but that it be limited only as defined in the claims.

What is claimed is:

1. A cardiac defibrillation system comprising:
    an epicardial electrode for making physical contact with the epicardium of a human heart from a position within the pericardial space of the heart;
    means for transvenously inserting said epicardial electrode into the pericardial space;
    an endocardial electrode for making physical contact with the endocardium of the heart; and
    means for selectively placing a momentary electrical potential between said epicardial and endocardial electrodes, said momentary electrical potential being sufficient to cause a momentary pulse of electrical energy to be delivered to the myocardial tissue intermediate said epicardial and endocardial electrodes; said electrical energy being sufficient to cause the myocardium of the heart to depolarize.

2. The cardiac defibrillation system, as set forth in claim 1, wherein said epicardial electrode comprises a plurality of spaced-apart epicardial electrode segments, each of said plurality of spaced-apart epicardial electrode segments being electrically connected to said means for placing a momentary electrical potential.

3. The cardiac defibrillation system, as set forth in claim 2, wherein said means for selectively placing a momentary electrical potential between said epicardial and endocardial electrodes includes means for adjusting the magnitude of the electrical potential placed between each of said plurality of spaced-apart epicardial electrode segments and said endocardial electrode, whereby the depolarization energy delivered to the heart is selectively directed to desired areas of the heart.

4. The cardiac defibrillation system, as set forth in claim 3, further including means for measuring a parameter related to the myocardial tissue between each of said spaced-apart epicardial electrode segments and said endocardial electrode, and wherein said means for adjusting the magnitude of the electrical potential placed between each of said plurality of spaced-apart electrode segments and said endocardial electrode includes means for adjusting the magnitude of the electrical potential as a function of said measured parameter.

5. The cardiac defibrillation system, as set forth in claim 4, wherein said parameter related to the myocardial tissue between said endocardial electrode and said plurality of spaced-apart epicardial electrode segments comprises impedance.

6. The cardiac defibrillation system, as set forth in claim 2, wherein said plurality of spaced-apart epicardial electrode segments in combination with said endocardial electrode concentrate the defibrillation energy in the left ventricle of the heart.

7. The cardiac defibrillation system, as set forth in claim 6, wherein said endocardial electrode is positioned proximate the septum of the heart within the right ventricle.

8. The cardiac defibrillation system, as set forth in claim 6, wherein said endocardial electrode comprises a plurality of spaced-apart endocardial electrode segments.

9. A cardiac defibrillation system comprising:
an endocardial electrode for making physical contact with the endocardium of a heart;
a plurality of spaced-apart epicardial electrodes for making physical contact with the epicardium of a human heart from a position within the pericardial space of the heart, said epicardial electrodes being transvenously insertable into the pericardial space; and
lead means for making electrical contact with said epicardial electrodes from a location removed from said heart, said lead means comprising an elongate flexible electrical conductor having an electrically insulating sheath therearound, said electrical conductor and sheath comprising a lead body, said spaced-apart electrodes being positioned near a distal end of said lead body, and further wherein said epicardial electrodes comprise a segment of conductive material having a circumference not substantially greater than the circumference of said lead body;
whereby an electrical potential of sufficient magnitude placed between said endocardial and epicardial electrodes by way of said electrical contact means triggers the depolarization of myocardial tissue proximate said electrodes.

10. The implantable defibrillation lead, as set forth in claim 9, further including a plurality of branches splitting off from the lead body near the distal end thereof, each of said branches having a length, at least one of said epicardial electrodes being positioned along said length of each branch.

11. The implantable defibrillation lead, as set forth in claim 9, wherein the distal end of said lead body comprises a loop, said loop being adapted to fit around a section of the heart, at least two of said plurality of spaced-apart epicardial electrodes being placed in electrical contact with said flexible electrical conductor at designated locations on said loop.

12. An implantable defibrillation lead system comprising:
a plurality of spaced-apart epicardial electrodes for making physical contact with the epicardium of a human heart from a position within the pericardial space of the heart, said epicardial electrodes being transvenously insertable into the pericardial space; and
a plurality of spaced-apart endocardial electrodes for making physical contact with the endocardium of the heart; and
first and second elongate flexible electrical conductors, each having an electrically insulating sheath therearound, said electrical conductor and sheath of each comprising a first and second lead body, respectively, said spaced-apart epicardial electrodes being positioned near a distal end of said first lead body, and said spaced-apart endocardial electrodes being positioned near a distal end of said second lead body; said spaced-apart epicardial electrodes comprising segments of conductive material in electrical contact with said first elongate flexible conductor and having a circumference not substantially greater than the circumference of said first lead body;
whereby an electrical potential of sufficient magnitude placed between said epicardial and endocardial electrodes through said first and second elongate flexible electrical conductors triggers the depolarization of myocardial tissue proximate said endocardial and epicardial electrodes.

13. The implantable defibrillation lead system, as set forth in claim 12, further including a plurality of branches splitting off from the first lead body near the distal end thereof, each of said branches having a length, at least one of said spaced-apart epicardial electrodes being positioned along the length of each of said branches.

14. The implantable defibrillation lead system, as set forth in claim 12, wherein the distal end of said first lead body comprises a loop, said loop being adapted to fit around a section of the heart, at least two of said plurality of spaced-apart epicardial electrodes being placed in electrical contact with said first flexible electrical conductor at designated locations on said loop.

15. An implantable defibrillation system, as set forth in claim 12, wherein said second lead body includes:
a plurality of branches splitting off from said second lead body near the distal end thereof, each of said branches having a length, at least one of said spaced-apart endocardial electrodes being positioned along the length of each branch; and
anchoring means for anchoring the distal end of said branches near the apex of the heart so as to place said spaced-apart endocardial electrodes in contact with the septum of the heart.

16. An implantable endocardial defibrillation lead system, as set forth in claim 15, wherein said anchoring means comprises screw-in helixes, fins or porous electrodes.

17. The implantable defibrillation lead system, as set forth in claim 15, further comprising:
resistance means intermediate said spaced-apart epicardial electrodes for placing an electrical resistance in series with said spaced-apart epicardial electrodes, whereby said first elongate flexible electrical conductor and said spaced-apart epicardial electrodes function as a first voltage divider network relative to said plurality of spaced-apart endocardial electrodes.

18. The implantable defibrillation lead system, set forth in claim 17, wherein said plurality of spaced-apart endocardial electrodes comprises:
a first endocardial electrode, directly connected to said second elongate flexible electrical conductor, said first electrical conductor having a first resistance; and
a second endocardial electrode, connected to said first endocardial electrode through a second resistance.

19. An implantable endocardial defibrillation lead comprising:
a plurality of spaced-apart endocardial electrodes for making physical and electrical contact proximate the septum of a heart;
a lead body having a plurality of branches spitting off from said body near a distal end thereof, each of said branches having a length, at least one of said plurality of endocardial electrodes being positioned along the length of each branch, and anchoring means for anchoring said branches near the apex of the heart so as to place said spaced-apart endocardial electrodes in contact with the septum of the heart, wherein said anchoring means comprises screw-in helixes, fins or porous electrodes.

20. A method of defibrillating a human heart comprising the steps of:
(a) transvenously inserting an epicardial electrode into the pericardial space surrounding the heart;
(b) positioning said epicardial electrode so that it makes electrical contact with a desired area of the epicardium;
(c) transvenously inserting an endocardial electrode inside of the heart;
(d) positioning said endocardial electrode so that it makes electrical contact with a desired area of the endocardium; and
(e) applying an electrical potential between said epicardial and endocardial electrodes; said electrical potential triggering the depolarization of myocardial tissue proximate said epicardial and endocardial electrodes.

21. The method of defibrillating a heart, as set forth in claim 20, wherein step (a) comprises transvenously inserting a plurality of spaced-apart epicardial electrodes into the pericardial space surrounding the heart.

22. The method of defibrillating a heart, as set forth in claim 21, wherein step (b) comprises positioning at least a plurality of said epicardial electrodes so that they contact epicardial tissue of the left ventricle.

23. The method of defibrillating a heart, as set forth in claim 22, wherein step (d) comprises positioning said endocardial electrode so that it contacts the septum of the heart from a position within the right ventricle.

24. The method of defibrillating a heart, as set forth in claim 23, wherein step (e) comprises applying an electrical potential of different magnitudes to different ones of said epicardial and endocardial electrodes for the purpose of directing different levels of defibrillation energy to selected areas of the heart.

25. The method of defibrillating a heart, as set forth in claim 23, wherein step (e) further comprises the steps of:
measuring impedance of the myocardial tissue between said epicardial and endocardial electrodes; and
adjusting the magnitude of the electrical potential on each electrode as a function of said measured impedance.

26. The method of defibrillating a heart, as set forth in claim 23, further comprising the steps of:
measuring impedance of the myocardial tissue between said epicardial and endocardial electrodes; and
repositioning said endocardial and epicardial electrodes based on said measured value of the myocardial tissue so that the defibrillation energy required to defibrillate the heart is minimized.

27. A method of defibrillating a human heart comprising the steps of:
(a) transvenously inserting a plurality of spaced-apart epicardial electrodes into the pericardial space surrounding the heart;
(b) positioning at least a plurality of said epicardial electrodes so that they contact epicardial tissue of the left ventricle;
(c) transvenously inserting an endocardial electrode inside of the heart;
(d) positioning said endocardial electrode so that it makes electrical contact with the septum of the heart from a position within the right ventricle; and
(e) applying an electrical potential between said epicardial and endocardial electrodes; said electrical potential triggering the depolarization of myocardial tissue proximate said epicardial and endocardial electrodes.

28. The method of defibrillating a heart, as set forth in claim 27, wherein step (e) comprises applying an electrical potential of different magnitudes to different ones of said epicardial and endocardial electrodes for the purpose of directing different levels of defibrillation energy to selected areas of the heart.

29. The method of defibrillating a heart, as set forth in claim 27, wherein step (e) further comprises the steps of:
measuring impedance of the myocardial tissue between said epicardial and endocardial electrodes; and
adjusting the magnitude of the electrical potential on each electrode as a function of said measured impedance.

30. The method of defibrillating a heart, as set forth in claim 27, further comprising the steps of:
measuring the impedance of the myocardial tissue between said epicardial and endocardial electrodes; and
repositioning said endocardial and epicardial electrodes based on said measured value of the myocardial tissue so that the defibrillation energy required to defibrillate the heart is minimized.

* * * * *